United States Patent [19]

Oda et al.

[11] 3,936,505

[45] Feb. 3, 1976

[54] PROCESS FOR PREPARING UNSATURATED ALDEHYDE HAVING THREE TO FOUR CARBON ATOMS

[75] Inventors: Yoshio Oda; Keiichi Uchida, both of Yokohama; Manabu Suhara, Tokyo; Takeshi Morimoto, Yokohama, all of Japan

[73] Assignee: Asahi Glass Company, Ltd., Tokyo, Japan

[22] Filed: Feb. 22, 1973

[21] Appl. No.: 334,727

[30] Foreign Application Priority Data

Feb. 22, 1972 Japan............................ 47-17653
Apr. 11, 1972 Japan............................ 47-35725
Apr. 17, 1972 Japan............................ 47-37800

[52] U.S. Cl............. 260/604 R; 252/437; 252/439; 252/458; 252/462; 252/465; 252/467; 252/468; 252/469; 252/470
[51] Int. Cl.²......................................... C07C 45/02
[58] Field of Search ..................... 260/604 R, 680 E

[56] References Cited
UNITED STATES PATENTS

| | | |
|---|---|---|
| 3,168,572 | 2/1965 | Voge et al...................... 260/604 R |
| 3,639,269 | 2/1972 | Koberstein et al............. 260/604 R |
| 3,716,496 | 2/1973 | Yoshino et al.................. 260/604 R |
| 3,778,386 | 12/1973 | Takenaka et al. ............. 260/604 R |
| 3,786,000 | 1/1974 | Liguni et al..................... 260/604 R |
| 3,790,502 | 2/1974 | Nemec et al.................... 260/604 R |

Primary Examiner—James O. Thomas, Jr.
Assistant Examiner—Nicky Chan
Attorney, Agent, or Firm—Oblon, Fisher, Spivak, McClelland & Maier

[57] ABSTRACT

An unsaturated aldehyde having three to four carbon atoms is prepared by reacting the corresponding olefin with molecular oxygen in the vapor phase at a temperature of from 350° to 520° C in the presence of a metal oxide catalyst comprising the metallic components: (a) molybdenum; (b) at least one metal selected from the group consisting of niobium and tantalum; and (c) at least one metal selected from the group consisting of tellurium, bismuth, cobalt, tungsten, indium, and titanium.

4 Claims, No Drawings

3,936,505

PROCESS FOR PREPARING UNSATURATED ALDEHYDE HAVING THREE TO FOUR CARBON ATOMS

BACKGROUND OF THE INVENTION

1. Field of the Invention

This invention relates to a process for preparing unsaturated aldehydes having three to four carbon atoms by oxidizing the corresponding olefin with molecular oxygen. More particularly, this invention relates to a process for preparing methacrolein in high yields by oxidizing isobutylene with molecular oxygen.

2. Description of the Prior Art

Various processes for preparing unsaturated aldehydes by the catalytic vapor phase oxidation of olefins having three to four carbon atoms with molecular oxygen in the presence of various catalysts have been proposed. In most of these processes, acrolein has been advantageously produced from propylene. However, it has been difficult to prepare methacrolein from isobutylene using similar processes. For example, it is known that acrolein can be prepared from propylene in a selectivity of more than 85% and an olefin conversion of 90 – 95% which is required for industrial production. If the process is used for the preparation of methacrolein from isobutylene, selectivities for methacrolein of up to 50% are obtained which is unsatisfactory for industrial purposes.

Even though propylene and isobutylene are very similar compounds and isobutylene is readily combustible, there is a substantial difference in the oxidative reactivity of the two compounds. However, it is expected that suitable catalysts can be found which exhibit high yields and selectiveties for the conversion of isobutylene to methacrolein.

A need, therefore, exists for a catalyst which will promote the oxidative reaction of isobutylene to give methacrolein in high yields and selectivity.

SUMMARY OF THE INVENTION

Accordingly, it is an object of this invention to provide a process for preparing unsaturated aldehydes having three to four carbon atoms in high yield.

It is another object of this invention to provide a process for preparing methacrolein in substantially high yields which have not been attained by conventional processes.

Yet another object of this invention is to provide a process for preparing higher yields of acrolein.

These objects and other objects of this invention as hereinafter will become more readily apparent can be attained by a process for preparing an unsaturated aldehyde having three to four carbon atoms by the oxidation of the corresponding olefin with molecular oxygen in the presence of a metal oxide catalyst containing the metallic components: (a) molybdenum; (b) at least one of niobium and tantalum; and (c) at least one of tellurium, bismuth, cobalt, tungsten, indium and titanium. The catalysts of this invention may also contain various nonessential components such as an oxide of an alkali metal, copper, silver, calcium, magnesium, cadmium, lead, arsenic, antimony, vanadium, chromium, iron, nickel, lanthanum, cerium, tin, phosphorous, boron and silicon to improve the activity of the catalyst.

DESCRIPTION OF THE PREFERRED EMBODIMENTS

The catalysts of this invention have the desired catalytic activity, only when the catalysts contain all of the essential components. If the catalysts lack one or two of the essential components, the activities of these catalysts will be relatively low, which will result in low yields of the desired unsaturated aldehydes, rendering the catalysts unsatisfactory for commercial applications. The preferred catalysts of the invention are characterized by the following empirical formula which, in part, contains 12 molybdenum atoms, $$Mo_{12} - X_x - Y_y - O_d$$

wherein X represents at least one of Nb and Ta: Y represents at least one of Te, Bi, Co, W In and Ti; $x$ is a number from 0.1 to 9, preferably 0.3 to 3; $y$ is a number from 0.2 to 12, preferably 0.5 to 5; and $d$, which is determined by the oxidation state of each component, is a number from about 36 to about 95 when each component is in a highly oxidized state.

When the catalysts of this invention contain the additional or nonessential components, the preferred empirical formula may be expressed as follows:

$$Mo_{12} - X_x - Y_y - Z_z - O_d$$

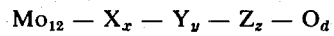

wherein X, Y, $x$ and $y$ are defined as before; Z represents at least one alkali metal (Li, Na, K), Cu, Ag, Ca, Mg, Cd, B, Si, Sn, Pb, P, As, Sb, V, Cr, Fe, Ni, La, Ce; $z$ is a number from 0.2 to 15, preferably 0.5 to 5; and $d$ is a number from about 36 to about 132 when each component is in a highly oxidized state.

Two improvements are noted in the catalysts when the non-essential components are present. The first improvement is in the conversion of the olefin and the second improvement is in the selectivities achieved of the desired unsaturated aldehydes. The degree of improvement in both cases depends upon the type of additional metallic component present in the catalyst. The improvements can be attained without decreasing the selectivity or the conversion. Selectivities are enhanced by the addition of Fe, Cu, Cr, Ag or Mg to the catalyst, while conversions are enhanced by the addition of Sb, As, alkali metal (Li, Na, K), Cd, Pb, Ce or Ca to the catalyst.

In one embodiment of the process according to this invention, desired unsaturated aldehydes can be prepared in substantially high yields with a mixed metal oxide catalyst consisting of the metallic components (a) Mo; (b) at least one of Nb and Ta; and (c) Bi. Preferably, the metallic components consist of (a) Mo; (b) at least one of Nb and Ta; (c) Bi; and (d) at least one alkali metal (Li, Na, K), Cu, Te, As, Sb and Fe. Preferably, the catalyst of the first embodiment has the empirical formula $$Mo_{12} - X_a - Bi_b - O_d$$

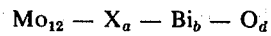

wherein X represents Nb or Ta; $a$ is a number from 0.1 to 9, preferably 0.3 to 3; $b$ is a number from 1 to 12, preferably 3 to 10; and $d$, which is determined by the oxidation state of the metallic components, is a number from about 37 to about 77 when each component is in a highly oxidized state. When at least one of the nonessential components is present in the catalyst such as an alkali metal, Cu, Te, As, Sb and Fe, the preferred empirical formula may be expressed as follows:

$$Mo_{12} - X_a - Bi_b - Y'_c - O_d$$

wherein X, $a$ and $b$ are defined as above; Y' represents at least one metal selected from the group consisting of an alkali metal, Cu, Te, As, Sb and Fe; $c$ is a number from 0.1 to 15, preferably 0.5 to 5; and $d$ is a number from about 37 to about 114 depending upon the oxidation states of the metal components.

In a second embodiment of the process of this invention, specific unsaturated aldehydes are prepared by reacting an olefin having three to four carbon atoms with molecular oxygen in the presence of a metal oxide catalyst, containing the metallic components (a) Mo; (b) at least one of Nb and Ta; and (c) Te. Preferably, the metallic components, (a) Mo; (b) at least one of Nb and Ta; (c) Te; and (d) at least one alkali metal (Li, Na, K), Cu, As, Sb, and Fe are used.

In the second embodiment of the invention it is preferable to use the catalyst having the empirical formula;

$$Mo_{12} - X_a - Te_e - O_d$$

wherein X is defined as before; $a$ is a number from 0.2 to 9, preferably 0.5 to 3; $e$ is a number from 0.2 to 5, preferably 0.5 to 3; and $d$ is a number from 37 to 76 when each metallic component is in a highly oxidized state. When at least one nonessential metallic component is present in the catalyst such as an alkali metal, Cu, As, Sb or Fe, the preferred empirical formula of the catalyst may be expressed as follows:

$$Mo_{12} - X_a - Te_e - Y''_f - O_d$$

wherein X, $a$ and $e$ are defined as above; Y'' represents at least one metal selected from the group consisting of an alkali metal, Cu, As, Sb, and Fe; $f$ is a number from 0.2 to 9, preferably 0.5 to 5; and $d$ is a number from 37 to 103 when each component is in a highly oxidized state.

The catalysts of this invention may be prepared by any one of several methods. Preferably, the catalysts may be prepared by concentrating a solution or a suspension containing the desired components and drying the resulting concentrate. Thereafter, preferably the dried product is calcined at a temperature from 400° to 600°C., especially 450° to 550°C., for about 1 to about 20 hours in air. Then, the calcined product is ground into a mesh size of 35 to 100, which is suitable for use. The prepared catalyst has a specific surface area of 0.1 to 50 m²/g.

In some cases, the catalysts are preferably supported on a suitable carrier, such as silica, silica-containing materials, silicon carbide, alumina and the like, in order to improve the physical properties of the catalysts. The amount of the carrier used is preferably in the range of 30 to 97% by weight based on the weight of the supported catalyst.

The exact chemical structure of the catalysts of this invention is not known. However, it can reasonably be presumed that the catalyst may be a homogeneous mixture of the oxides and/or complex oxides of all the components.

The starting materials of each component used in the preparation of the catalysts are listed as follows: Suitable sources of molybdenum include ortho-, meta- or paramolybdic acid, ortho, meta- or paramolybdates, heteromolybdic acid, heteromolybdates, molybdenum oxide and the like. Suitable sources of niobium and tantalum include niobium oxide, niobium hydroxide, niobium oxalate, tantalum oxide, tantalum hydroxide, tantalum oxalate and the like. Suitable sources of bismuth include bismuth oxide, bismuth hydroxide, bismuth nitrate and the like. Suitable sources of chromium include chromium nitrate, chromium oxide, chromates, bichromates and the like. Suitable sources of tungsten include ammonium paratungstate, tungsten oxide, tungstic acid and salts thereof and the like. Suitable sources of tin, phosphorous, antimony, tellurium, cobalt, indium and titanium include tin oxide, tin hydroxide, tin chloride, phosphoric acid, and salts thereof, antimony oxide, antimony chloride, telluric acid and salts thereof, tellurium oxide, cobalt oxide, cobalt nitrate, indium oxide, indium nitrate, titanium chloride, titanium oxide, titanium hydroxide and the like. Suitable sources of an alkali metal, Cu, Ag, Mg, Ca, Cd, Pb, As, V, Fe, Ni, La, Si, B, Ce and Th include the oxides, nitrates, hydroxides and ammonium salts thereof.

In the preparation of an unsaturated aldehyde having three or four carbon atoms from the corresponding olefin having three or four carbon atoms, the reaction temperature may vary within the range from 350°C. to 520°C., preferably 430°C. to 500°C., and the reaction pressure may vary within the range from 1 to 10 atmospheres absolute, preferably 1 to 5 atmospheres absolute. When the reaction pressure is in the upper regions of said range, the reaction temperature may be somewhat lower within the indicated temperature range. The apparent contact time may usually vary from 0.1 to 20 seconds, preferably 0.5 to 5 seconds.

The mole ratio of oxygen to olefin in the feed gas supplied to the reactor usually ranges from 3 : 1 to 1 : 5, especially 3 : 1 to 1 : 1. The oxygen used in the reaction can be any source of molecular oxygen under the reaction conditions with air being the most economical oxygen source. Sometimes, the yield of the desired unsaturated aldehyde is increased by admitting steam to the gaseous reactant mixture. The concentration of steam admitted is preferably in the range of from 5 to 60%, especially 10 to 30%. It is also possible to add an inert gas such as nitrogen or saturated hydrocarbons such as methane, ethane, propane and butane, to said gaseous reactant mixture. Any type of reactor suitable for vapor phase oxidation may be employed in the operation of this invention. Suitable reactors include continuously operating, intermittently operating, solid bed and fluid bed reactors.

In accordance with the process of this invention, the preparation of methacrolein from isobutylene can be successfully conducted on an industrial scale. Therefore, development of new methods of application of methacrolein should be persued, since methacrolein can be economically and easily prepared.

Having generally described the invention, a more complete understanding can be obtained by reference to certain specific examples, which are intended for purpose of illustration only and are not intended to be limiting unless otherwise specified.

The following definitions apply to olefin conversion and to the selectivity of unsaturated aldehyde. All of the analyses were conducted by means of gas chromatography.

$$\text{Olefin Conversion (\%)} = \frac{\text{Olefin reacted (mole)}}{\text{Olefin fed (mole)}} \times 100$$

Selectivity of $$\text{unsaturated aldehyde} = \frac{\text{Unsaturated aldehyde}}{\text{Olefin reacted (mole)}} \times 100$$

The atomic ratio of the metallic components of the catalysts with the exception of the oxygen ratios are shown in the columns of the Tables in the Examples and References.

EXAMPLE 1

A solution of 655 g of bismuth nitrate ($Bi(NO_3)_3$) in a mixture of 600 ml of water and 120 ml of 60% nitric acid was added with vigorous stirring to a solution of 318 g of ammonium molybdenate in 600 ml of water. A suspension of 19.9 g of niobium oxide ($Nb_2O_5$) in a mixture of 300 ml of water and 200 ml of 60% nitric acid, was added with stirring, to the heated slurry. The mixture was condensed and dried. The resulting cake was dried at 120° C. for 16 hours and was calcined at 500° C. for 3 hours so that a solid metal oxide mixture having the empirical formula $Mo_{12}Bi_9Nb_1$ (oxygen omitted) was obtained. The solid oxide was passed through a sieve to yield catalyst particles having a 35 – 100 mesh size. A 2 ml quantity of the catalyst was uniformly admixed with 4 ml of silicon carbide having an 80 mesh particle size. A U-shaped stainless steel reaction tube with an inner diameter of 6 mm was filled with the fluid. The reaction tube was put into a molten salt bath heated at 460° C. A gaseous reactant mixture consisting of 85% nitrogen by volume, 10% oxygen by volume, and 5% isobutylene by volume was passed through the reaction tube with a contact time of 1 second. The results obtained are shown below:

| | |
|---|---|
| Conversion of isobutylene | 93.8% |
| Selectivity of methacrolein | 74.4% |
| Combustion rate (CO + $CO_2$) | 20.3% |

EXAMPLE 2

In accordance with the process of Example 1, with the exception that 33.2 g of tantalum oxide ($Ta_2O_5$) was used instead of niobium oxide, an oxide catalyst having the empirical formula $Mo_{12}Bi_9Ta_1$ (oxygen omitted) was prepared. The gaseous reactant mixture was reacted in accordance with the process of Example 1. The results obtained are shown below.

| | |
|---|---|
| Conversion of isobutylene | 91.1% |
| Selectivity of methacrolein | 72.0% |
| Combustion rate (CO + $CO_2$) | 23.5% |

EXAMPLES 3 – 10

In accordance with the process of Examples 1 to 2 the metal oxide catalysts shown in Table I were used to catalyze the oxidation of isobutylene to methacrolein. The results obtained are shown in Table I.

TABLE I

| Example No. | Catalyst System | isobutylene conversion (%) | methacrolein selectivity (%) | Combustion rate(CO+$CO_2$) (%) |
|---|---|---|---|---|
| 3 | $Mo_{12}Bi_4Nb_1$ | 82.3 | 75.0 | 19.7 |
| 4 | $Mo_{12}Bi_1Nb_1$ | 53.2 | 79.8 | 15.5 |
| 5 | $Mo_{12}Bi_9Nb_3$ | 96.1 | 74.0 | 22.7 |
| 6 | $Mo_{12}Bi_9Nb_7$ | 95.6 | 73.5 | 23.1 |
| 7 | $Mo_{12}Bi_9Nb_{0.3}$ | 92.2 | 73.6 | 19.9 |
| 8 | $Mo_{12}Bi_4Ta_1$ | 78.7 | 72.4 | 24.2 |
| 9 | $Mo_{12}Bi_9Ta_3$ | 92.3 | 73.6 | 22.2 |
| 10 | $Mo_{12}Bi_9Ta_{0.5}Nb_{0.5}$ | 92.6 | 73.1 | 20.8 |

REFERENCE I

In accordance with the process of Example 1, the metal oxide catalysts shown in Table II were used to catalyze the oxidation of isobutylene to methacrolein. The results obtained are shown in Table II.

TABLE II

| Catalyst System | Isobutylene conversion (%) | Methacrolein selectivity (%) | Combustion rate (CO+$CO_2$) (%) |
|---|---|---|---|
| $Mo_{12}Bi_9$ | 71.5 | 69.9 | 24.8 |
| $Mo_{12}Nb_3$ | 82.6 | 65.8 | 29.1 |

EXAMPLE 11

A suspension of 2.66 g of niobium oxide in 10 ml of water was added with vigorous stirring to a solution of 42.4 g of ammonium paramolybdenate in 100 ml of water until a slurry was achieved. A 5 ml quantity of nitric acid was diluted with 20 ml of water, added to the slurry and heated with stirring. A 6.35 g amount of tellurium oxide (II) powder was added to the slurry, heated under stirring, condensed and dried. The resulting cake was dried at 120° C. for 12 hours and was calcined at 500° C. for 3 hours so that a solid metal oxide having the empirical formula $Mo_{12}Nb_1Te_2$ (oxygen omitted) was obtained. The solid oxide was crushed and was passed through a sieve to yield catalyst particles having a 35 – 100 mesh size. A 2 ml amount of the sieved catalyst was uniformly admixed with 4 ml of silicon carbide having an 80 mesh particle size. A U-shaped, stainless steel reaction tube with an inner diameter of 6 mm was filled with the catalyst. The reaction tube was immersed in a molten salt bath heated at 435° C. A gaseous reactant mixture consisting of 85% nitrogen by volume, 10% oxygen by volume, and 5% isobutylene by volume was passed through the reaction tube with a contact time of 1 second. The conversion of isobutylene was 82.3% with a 70.5% selectivity of methacrolein and a combustion rate (CO + $CO_2$) of 23.0%.

EXAMPLES 12 – 16

The gaseous mixture was reacted in accordance with the process of Example 11 except that metal oxide catalysts having the empirical formulas shown in Table V were used. The results obtained are shown in Table III.

TABLE III

| Example No. | Catalyst System | Isobutylene Conversion (%) | Methacrolein Selectivity (%) | Combustion rate ($CO + CO_2$) (%) |
|---|---|---|---|---|
| 12 | $Mo_{12}Nb_1Te_1$ | 80.1 | 70.7 | 24.9 |
| 13 | $Mo_{12}Nb_3Te_5$ | 76.2 | 68.8 | 25.5 |
| 14 | $Mo_{12}Nb_5Te_2$ | 87.0 | 68.5 | 29.0 |
| 15 | $Mo_{12}Nb_{0.5}Te_1$ | 51.4 | 74.3 | 21.1 |
| 16 | $Mo_{12}Nb_1Te_{0.5}$ | 69.4 | 69.0 | 26.6 |

EXAMPLES 17 – 20

The gaseous mixture was reacted in accordance with the process of Example 11 except that 11.6 g of cobalt nitrate ($Co(NO_3)_2 \cdot 6H_2O$), 10.4 g of ammonium tungstate ($5(NH_4)_2O \cdot 12WO_3 \cdot 5H_2O$), 14.2 g of indium nitrate ($In(NO_3)_3 \cdot 3H_2O$), or 7.5 g of titanium tetrachloride were used instead of tellurium oxide in order to prepare metal oxide catalysts having the empirical formulas shown in Table IV. The results obtained are shown in Table IV.

TABLE IV

| Example No. | Catalyst system | Isobutylene Conversion (%) | Methacrolein Selectivity (%) | Combustion rate ($CO + CO_2$) (%) |
|---|---|---|---|---|
| 17 | $Mo_{12}Nb_1Co_2$ | 75.6 | 72.9 | 25.0 |
| 18 | $Mo_{12}Nb_1W_2$ | 76.1 | 71.1 | 23.4 |
| 19 | $Mo_{12}Nb_1In_2$ | 70.6 | 77.5 | 21.3 |
| 20 | $Mo_{12}Nb_1Ti_2$ | 73.2 | 75.8 | 20.4 |

EXAMPLES 21 – 24

The gaseous mixture was reacted in accordance with the process of Examples 17 – 20 except that metal oxide catalysts having the empirical formulas in Table V were used. The results obtained are shown in Table V.

TABLE V

| Example No. | Catalyst system | Isobutylene Conversion (%) | Methacrolein Selectivity (%) | Combustion rate ($CO + CO_2$) (%) |
|---|---|---|---|---|
| 21 | $Mo_{12}Nb_{0.5}Co_5$ | 83.0 | 69.0 | 24.2 |
| 22 | $Mo_{12}Nb_2W_1$ | 79.7 | 75.2 | 23.5 |
| 23 | $Mo_{12}Nb_1In_5$ | 65.3 | 81.0 | 12.8 |
| 24 | $Mo_{12}Nb_{0.5}Ti_4$ | 71.2 | 72.6 | 24.7 |

EXAMPLE 25

The gaseous mixture was reacted in accordance with the process of Example 11, except that 4.42 g of tantalum oxide was used instead of niobium oxide in order to prepare metal oxide catalysts having the empirical formula, $Mo_{12}Ta_{12}Te_{12}$ (oxygen omitted). The results of the experiment gave an 81.8% conversion of isobutylene, a 67.3% selectivity of methacrolein and a combustion rate of 25.6%.

EXAMPLES 26 – 28

The gaseous mixture was reacted in accordance with the process of Example 25 except that metal oxide catalysts having the empirical formulas shown in Table VI were used. The results obtained are shown in Table VI.

TABLE VI

| Example No. | Catalyst system | Isobutylene Conversion (%) | Methacrolein Selectivity (%) | Combustion rate ($CO + CO_2$) (%) |
|---|---|---|---|---|
| 26 | $Mo_{12}Ta_1Te_1$ | 82.6 | 68.3 | 25.5 |
| 27 | $Mo_{12}Ta_5Te_5$ | 79.1 | 70.8 | 21.4 |
| 28 | $Mo_{12}Ta_3Te_2$ | 87.0 | 65.2 | 27.8 |

EXAMPLES 29 – 32

The gaseous mixture was reacted in accordance with the process of Example 11 except that metal oxide catalysts having the empirical formulas shown in Table VII were used. The results obtained are shown in Table VII.

TABLE VII

| Example No. | Catalyst system | Isobutylene Conversion (%) | Methacrolein Selectivity (%) | Combustion rate ($CO + CO_2$) (%) |
|---|---|---|---|---|
| 29 | $Mo_{12}Ta_1Co_2$ | 77.9 | 71.0 | 21.8 |
| 30 | $Mo_{12}Ta_2W_1$ | 80.5 | 66.1 | 30.7 |
| 31 | $Mo_{12}Ta_1In_5$ | 70.4 | 75.3 | 20.2 |
| 32 | $Mo_{12}Ta_1Ti_2$ | 76.2 | 70.3 | 27.9 |

REFERENCES II - 1 – 8

The gaseous mixture was reacted in accordance with the process of Example 11, except that the metal oxide catalysts having the empirical formulas shown in Table VIII were used. The results obtained are shown in Table VIII.

TABLE VIII

| Reference No. | Catalyst system | Isobutylene Conversion (%) | Methacrolein Selectivity (%) | Combustion rate (CO + CO$_2$) (%) |
|---|---|---|---|---|
| II-1 | Mo$_{12}$Te$_2$ | 19.9 | 72.6 | 22.5 |
| II-2 | Mo$_{12}$Nb$_1$ | 65.2 | 61.0 | 28.9 |
| II-3 | Mo$_{12}$Ta$_1$ | 67.1 | 64.4 | 29.3 |
| II-4 | Mo$_{12}$W$_2$ | 43.0 | 60.1 | 27.7 |
| II-5 | Mo$_{12}$Co$_2$ | 48.9 | 50.8 | 41.5 |
| II-6 | Mo$_{12}$In$_2$ | 27.2 | 69.6 | 27.4 |
| II-7 | Mo$_{12}$Nb$_1$P$_1$ | 18.0 | 40.1 | 55.6 |
| II-8 | Mo$_{12}$Nb$_1$Sb$_2$ | 27.5 | 49.7 | 46.3 |

EXAMPLE 33

A solution of 655 g of bismuth nitrate (Bi(NO$_3$)$_3$.5-H$_2$O) in a mixture of 600 ml of water and 120 ml of 60% nitric acid was added with vigorous stirring to a solution of 318 g of ammonium paramolybdenate in 600 ml of water. A 23.9 g amount of tellurium oxide (TeO$_2$) powder was slowly added to the resulting heated slurry. A suspension of 19.9 g of niobium oxide (Nb$_2$O$_5$) in a mixture of 200 ml of water and 19.9 g of nitric acid was added to the slurry. The mixture was condensed and dried.

The resulting metal oxide cake was dried at 120° C. for 16 hours and then was calcined at 500° C. for 3 hours to form a solid metal oxide catalyst having an empirical formula of Mo$_{12}$Bi$_9$Nb$_1$Te$_1$ (oxygen omitted). The solid metal oxide particles were passed through a sieve to give a catalyst with a 35 – 100 mesh particle size. The gaseous mixture was reacted over the catalyst in accordance with the process of Example 1. The results obtained are shown below.

| | |
|---|---|
| Conversion of isobutylene | 88.3% |
| Selectivity of methacrolein | 83.6% |
| Combustion rate (CO + CO$_2$) | 14.0% |

EXAMPLE 34

The gaseous mixture was reacted in accordance with the process of Example 33, except that a catalyst was used which had the empirical formula Mo$_{12}$Bi$_9$Ta$_1$Te$_1$ (oxygen omitted). The catalyst was prepared as described in Example 33 except that niobium oxide was replaced with 33.2 g of tantalum oxide (Ta$_2$O$_5$). The results obtained are shown below.

| | |
|---|---|
| Conversion of isobutylene | 87.0% |
| Selectivity of methacrolein | 73.9% |
| Combustion rate (CO + CO$_2$) | 21.2% |

EXAMPLES 35 – 41

The gaseous mixture was reacted in accordance with the processes of Examples 33 and 34, except that the catalysts were prepared by substituting a solution of 60 g of chromium nitrate (Cr(NO$_3$)$_3$.9H$_2$O) in 500 ml of water, 39.2 g of ammonium paratungstate powder, 22.6 g of tin oxide (SnO$_2$) powder in a solution of 17.3 g of 85% phosphoric acid in 100 ml of water; or 21.8 g of antimony oxide (Sb$_2$O$_3$) powder in the place of tellurium oxide in the metal oxide catalysts so as to form catalysts with the empirical formulas shown in Table IX. The results obtained are shown in Table IX.

TABLE IX

| Example No. | Catalyst system | Isobutylene Conversion (%) | Methacrolein Selectivity (%) | Combustion rate (CO + CO$_2$) (%) |
|---|---|---|---|---|
| 35 | Mo$_{12}$Bi$_9$Nb$_1$Cr$_1$ | 88.6 | 79.0 | 16.1 |
| 36 | Mo$_{12}$Bi$_9$Nb$_1$W$_1$ | 78.9 | 85.2 | 10.7 |
| 37 | Mo$_{12}$Bi$_9$Nb$_1$Sn$_1$ | 91.8 | 78.8 | 17.0 |
| 38 | Mo$_{12}$Bi$_9$Nb$_1$P$_1$ | 90.5 | 78.3 | 16.6 |
| 39 | Mo$_{12}$Bi$_9$Nb$_1$Sb$_1$ | 87.1 | 80.4 | 15.3 |
| 40 | Mo$_{12}$Bi$_9$Ta$_1$W$_1$ | 96.6 | 71.7 | 22.3 |
| 41 | Mo$_{12}$Bi$_9$Ta$_1$Sb$_1$ | 76.0 | 78.3 | 16.5 |

EXAMPLES 42 – 57

In accordance with the processes of Examples 33 – 40, metal oxide catalysts having the empirical formulas shown in Table X were prepared. The gaseous mixture was reacted over the catalysts in accordance with the process of Example 1. The results obtained are shown in Table X.

TABLE X

| Example No. | Catalyst system | Isobutylene Conversion (%) | Methacrolein Selectivity (%) | Combustion rate (CO + CO$_2$) (%) |
|---|---|---|---|---|
| 42 | Mo$_{12}$Bi$_9$Nb$_1$Te$_3$ | 86.3 | 82.1 | 14.3 |
| 43 | Mo$_{12}$Bi$_9$Ta$_1$Te$_7$ | 62.9 | 85.7 | 10.8 |
| 44 | Mo$_{12}$Bi$_9$Nb$_3$Te$_1$ | 95.0 | 76.2 | 18.4 |
| 45 | Mo$_{12}$Bi$_1$Nb$_3$Te$_1$ | 85.6 | 73.5 | 22.2 |
| 46 | Mo$_{12}$Bi$_9$Ta$_{0.3}$Te$_1$ | 86.2 | 82.3 | 12.6 |
| 47 | Mo$_{12}$Bi$_9$Nb$_1$Cr$_5$ | 94.8 | 75.4 | 19.9 |
| 48 | Mo$_{12}$Bi$_1$Nb$_1$Cr$_5$ | 79.2 | 74.4 | 21.3 |
| 49 | Mo$_{12}$Bi$_9$Ta$_1$W$_5$ | 83.7 | 81.6 | 14.7 |
| 50 | Mo$_{12}$Bi$_9$Nb$_5$W$_1$ | 92.0 | 80.8 | 14.8 |
| 51 | Mo$_{12}$Bi$_9$Nb$_1$W$_{0.5}$ | 87.7 | 82.2 | 16.2 |
| 52 | Mo$_{12}$Bi$_9$Ta$_1$P$_5$ | 60.3 | 79.8 | 16.1 |

TABLE X-continued

| Example No. | Catalyst system | Isobutylene Conversion (%) | Methacrolein Selectivity (%) | Combustion rate (CO + CO$_2$) (%) |
|---|---|---|---|---|
| 53 | Mo$_{12}$Bi$_9$Nb$_1$Sb$_5$ | 65.1 | 87.6 | 9.5 |
| 54 | Mo$_{12}$Bi$_9$Ta$_5$Sb$_1$ | 89.4 | 82.0 | 13.1 |
| 55 | Mo$_{12}$Bi$_9$Nb$_3$Sb$_5$ | 85.3 | 85.1 | 9.8 |
| 56 | Mo$_{12}$Bi$_9$Nb$_1$Sb$_{0.5}$Te$_{0.5}$ | 89.8 | 81.3 | 17.3 |
| 57 | Mo$_{12}$Bi$_9$Ta$_1$Te$_{0.5}$W$_{0.5}$ | 92.3 | 79.8 | 16.3 |

EXAMPLES 58 – 65

In accordance with the processes of Examples 1 – 10 and 33, metal oxide catalysts having the empirical formulas shown in Table XI were prepared. A gaseous mixture was passed over the catalyst in accordance with the process of Example 1, except that propylene was used instead of isobutylene and the reaction temperature was maintained at 470° C. The results obtained are shown in Table XI.

TABLE XI

| Example No. | Catalyst system | Propylene Conversion (%) | Acrolein Selectivity (%) | Combustion rate (CO + CO$_2$) (%) |
|---|---|---|---|---|
| 58 | Mo$_{12}$Bi$_9$Nb$_1$ | 95.3 | 79.1 | 13.8 |
| 59 | Mo$_{12}$Bi$_9$Ta$_1$ | 90.5 | 78.9 | 14.3 |
| 60 | Mo$_{12}$Bi$_9$Nb$_1$Te$_1$ | 93.7 | 87.0 | 9.4 |
| 61 | Mo$_{12}$Bi$_9$Ta$_1$Cr$_1$ | 94.4 | 85.7 | 11.5 |
| 62 | Mo$_{12}$Bi$_9$Ta$_1$W$_1$ | 90.3 | 89.2 | 7.9 |
| 63 | Mo$_{12}$Bi$_9$Ta$_1$Sn$_1$ | 98.2 | 82.6 | 14.0 |
| 64 | Mo$_{12}$Bi$_9$Ta$_1$P$_1$ | 93.8 | 84.4 | 12.2 |
| 65 | Mo$_{12}$Bi$_9$Nb$_1$Sb$_1$ | 93.0 | 86.9 | 10.3 |

EXAMPLES 66 – 70

The gaseous mixture was reacted in accordance with the process of Examples 11 – 32 except that metal oxide catalysts having the empirical formulas shown in Table XII were used. The results obtained are shown in Table XII.

TABLE XII

| Example No. | Catalyst system | Isobutylene Conversion (%) | Methacrolein Selectivity (%) | Combustion rate (CO + CO$_2$) (%) |
|---|---|---|---|---|
| 66 | Mo$_{12}$Nb$_1$Te$_{0.5}$Ta$_2$ | 80.3 | 70.1 | 26.3 |
| 67 | Mo$_{12}$Nb$_1$Te$_2$In$_2$ | 75.7 | 80.5 | 11.0 |
| 68 | Mo$_{12}$Nb$_1$Te$_2$Co$_2$ | 94.4 | 76.0 | 19.4 |
| 69 | Mo$_{12}$Ta$_1$Co$_1$Ti$_1$ | 82.8 | 71.2 | 27.5 |
| 70 | Mo$_{12}$Ta$_1$Te$_2$W$_2$ | 99.8 | 75.6 | 20.7 |

EXAMPLE 71

A suspension of 2.66 g of niobium oxide (Nb$_2$O$_5$) in 10 ml of water was added with vigorous stirring to a solution of 42.4 g of ammonium paramolybdenate in 100 ml of water until a slurry was obtained. A 5 ml quantity of nitric acid was diluted with 20 ml of water, and the diluted acid was added to the slurry and heated with stirring. A 5.80 g amount of antimony oxide (Sb$_2$O$_3$) powder and 6.35 g of tellurium oxide (TeO$_2$) were added to the slurry, heated with stirring, condensed and dried. The resulting cake was dried at 120° C. for 12 hours and then was calcined at 500° C. for 3 hours until a solid oxide having the empirical formula Mo$_{12}$Nb$_1$Te$_2$Sb$_2$ (oxygen omitted) was obtained.

The solid metal oxide catalyst was crused and was passed through a sieve to yield a catalyst having a 35 – 100 mesh particle size. A 2 ml amount of the sieved catalyst was uniformly admixed with 4 ml of silicon carbide having an 80 mesh particle size. A U-shaped, stainless steel reaction tube having an inner diameter of 6 mm was filled with the catalyst. The reaction tube was placed in a molten salt bath at a temperature of 435° C.

A gaseous reactant mixture consisting of 85% nitrogen by volume, 10% oxygen by volume, and 5% isobutylene by volume was passed through the reaction tube with a contact time of 1 second. The results obtained indicated a 71.6% conversion of isobutylene, an 89.5% selectivity of methacrolein and a 6.1% combustion rate (CO + CO$_2$).

EXAMPLES 72 – 79

The gaseous mixture was reacted in accordance with the process of Example 71, except that metal oxide catalysts having the empirical formulas shown in Table XIII were prepared by adding a solution or suspension of 4.60 g of arsenic oxide (As$_2$O$_5$), 0.96 g of lithium hydroxide (LiOH), 1.60 g of sodium hydroxide (NaOH), 2.24 g of potassium hydroxide (KOH), 12.3 g of cadmium nitrate (Cd(NO$_3$)$_2$·4H$_2$O), 6.64 g of lead nitrate (Pb(NO$_3$)$_2$), 17.4 g of ammonium cerium nitrate (Ce(NO$_3$)$_4$·2NH$_4$NO$_3$·2H$_2$O) or 2.96 g of calcium hydroxide (Ca(OH)$_2$ in 50 ml of water in place of antimony oxide (Sb$_2$O$_3$) to the other metal oxide components. The results obtained are shown in Table XIII. It was found that the selectivity of methacrolein was high when these metal oxide catalysts were used.

TABLE XIII

| Example No. | Catalyst system | Isobutylene Conversion (%) | Methacrolein Selectivity (%) | Combustion ($CO+CO_2$) rate (%) |
|---|---|---|---|---|
| 72 | $Mo_{12}Nb_1Te_2As_2$ | 71.4 | 82.9 | 14.7 |
| 73 | $Mo_{12}Nb_1Te_2Li_2$ | 82.1 | 80.3 | 14.8 |
| 74 | $Mo_{12}Nb_1Te_2Na_2$ | 77.8 | 83.4 | 10.2 |
| 75 | $Mo_{12}Nb_1Te_2K_2$ | 80.1 | 81.9 | 13.0 |
| 76 | $Mo_{12}Nb_1Te_2Cd_2$ | 83.6 | 77.3 | 21.8 |
| 77 | $Mo_{12}Nb_1Te_2Pb_2$ | 68.4 | 87.5 | 10.4 |
| 78 | $Mo_{12}Nb_1Te_2Ce_2$ | 72.6 | 82.7 | 14.1 |
| 79 | $Mo_{12}Nb_1Te_2Ca_2$ | 81.5 | 81.6 | 13.9 |

EXAMPLES 80 – 84

The gaseous mixture was reacted in accordance with the process of Example 76 except that metal oxide catalysts having the empirical formulas shown in Table XIV were used. These catalysts were prepared by adding a solution or suspension of 3.20 g of iron oxide ($Fe_2O_3$); 9.66 g of copper nitrate ($Cu(NO_3)_2 \cdot 3H_2O$); 16.0 g of chromium nitrate ($Cr(NO_3)_3 \cdot 9H_2O$); 6.80 g of silver nitrate ($AgNO_3$); or 10.3 g of magnesium nitrate ($Mg(NO_3)_2 \cdot 6H_2O$) in 50 ml of water to the other metal oxide components instead of antimony oxide. The results obtained are shown in Table XIV. It was found that the conversion of isobutylene was high when these oxide catalysts were used.

TABLE XIV

| Example No. | Catalyst System | Isobutylene Conversion (%) | Methacrolein Selectivity (%) | Combustion rate ($CO + CO_2$) (%) |
|---|---|---|---|---|
| 80 | $Mo_{12}Nb_1Te_2Fe_2$ | 96.1 | 75.8 | 20.2 |
| 81 | $Mo_{12}Nb_1Te_2Cu_2$ | 93.5 | 76.6 | 21.4 |
| 82 | $Mo_{12}Nb_1Te_2Cr_2$ | 95.3 | 70.3 | 23.8 |
| 83 | $Mo_{12}Nb_1Te_2Ag_2$ | 98.7 | 70.3 | 25.0 |
| 84 | $Mo_{12}Nb_1Te_2Mg_2$ | 97.8 | 76.3 | 21.0 |

EXAMPLES 85 – 88

The gaseous mixture was reacted in accordance with the process of Example 71, except that metal oxide catalysts having the empirical formulas shown in Table XV were used. These catalysts were prepared by adding a solution or suspension of 11.6 g of nickel nitrate ($Ni(NO_3)_2 \cdot 6H_2O$); 4.68 g of ammonium vanadate ($NH_4VO_3$); 17.3 g of lanthanum nitrate ($La(NO_3)_3 \cdot 6H_2O$); or 22.1 g of thorium nitrate ($Th(NO_3)_4 \cdot 4H_2O$) in 50 ml of water to the other metal oxide components instead of antimony oxide. The results obtained are shown in Table XV.

TABLE XV

| Example No. | Catalyst system | Isobutylene Conversion (%) | Methacrolein Selectivity (%) | Combustion rate ($CO + CO_2$) (%) |
|---|---|---|---|---|
| 85 | $Mo_{12}Nb_1Te_2Ni_2$ | 87.9 | 74.5 | 24.9 |
| 86 | $Mo_{12}Nb_1Te_2V_2$ | 85.2 | 73.0 | 20.5 |
| 87 | $Mo_{12}Nb_1Te_2La_2$ | 84.3 | 77.4 | 20.8 |
| 88 | $Mo_{12}Nb_1Te_2Th_2$ | 88.2 | 73.6 | 24.3 |

EXAMPLES 89 – 102

The gaseous mixture was reacted in accordance with the process of Examples 71 except that metal oxide catalysts having the empirical formulas shown in Table XVI were used. These catalysts were prepared in accordance with the process of Examples 71 – 79. The results obtained are shown in Table XVI.

TABLE XVI

| Example No. | Catalyst system | Isobutylene Conversion (%) | Methacrolein Selectivity (%) | Combustion rate ($CO + CO_2$) (%) |
|---|---|---|---|---|
| 89 | $Mo_{12}Nb_1Te_1Sb_{0.5}$ | 78.1 | 80.6 | 13.6 |
| 90 | $Mo_{12}Nb_1Te_1Sb_2$ | 68.0 | 87.0 | 8.3 |
| 91 | $Mo_{12}Nb_3Te_1Sb_2$ | 85.9 | 77.8 | 21.8 |
| 92 | $Mo_{12}Nb_1Te_1As_5$ | 65.9 | 85.5 | 11.4 |
| 93 | $Mo_{12}Nb_3Te_2As_3$ | 77.0 | 83.9 | 13.8 |
| 94 | $Mo_{12}Nb_1Te_2Li_{0.5}$ | 80.5 | 79.3 | 14.1 |
| 95 | $Mo_{12}Nb_3Te_2Na_1$ | 85.2 | 80.3 | 13.8 |
| 96 | $Mo_{12}Nb_1Te_1Na_2$ | 83.4 | 82.7 | 10.6 |
| 97 | $Mo_{12}Nb_1Te_5K_{0.5}$ | 77.4 | 84.7 | 10.5 |
| 98 | $Mo_{12}Nb_1Te_1Cd_5$ | 78.1 | 79.2 | 16.0 |
| 99 | $Mo_{12}Nb_1Te_2Cd_{0.5}$ | 82.5 | 74.8 | 17.5 |
| 100 | $Mo_{12}Nb_1Te_2Pb_{0.5}$ | 75.2 | 83.1 | 16.2 |
| 101 | $Mo_{12}Nb_2Te_2Ce_1$ | 75.5 | 80.4 | 18.4 |
| 102 | $Mo_{12}Nb_1Te_2Ca_3$ | 75.2 | 83.1 | 16.2 |

EXAMPLES 103 – 112

The gaseous mixture was reacted in accordance with the process of Example 71, except that metal oxide catalysts having the empirical formulas shown in Table XVII were used. These catalysts were prepared in accordance with the process of Examples 80 – 84. The results obtained are shown in Table XVII.

TABLE XVII

| Example No. | Catalyst system | Isobutylene Conversion (%) | Methacrolein Selectivity (%) | Combustion rate (CO + CO$_2$) (%) |
|---|---|---|---|---|
| 103 | Mo$_{12}$Nb$_1$Te$_2$Fe$_{0.5}$ | 88.4 | 78.2 | 15.1 |
| 104 | Mo$_{12}$Nb$_1$Te$_5$Fe$_5$Sb | 90.1 | 74.2 | 20.9 |
| 105 | Mo$_{12}$Nb$_{0.5}$Te$_2$Fe$_2$ | 88.0 | 76.5 | 21.9 |
| 106 | Mo$_{12}$Nb$_1$Te$_1$Cu$_1$ | 91.7 | 78.0 | 20.9 |
| 107 | Mo$_{12}$Nb$_3$Te$_4$Cu$_3$ | 89.1 | 72.6 | 25.3 |
| 108 | Mo$_{12}$Nb$_2$Te$_2$Cr$_1$ | 94.3 | 75.2 | 22.0 |
| 109 | Mo$_{12}$Nb$_2$Te$_2$Cr$_{0.5}$ | 91.7 | 77.9 | 21.4 |
| 110 | Mo$_{12}$Nb$_1$Te$_2$Ag$_1$ | 96.7 | 70.9 | 23.7 |
| 111 | Mo$_{12}$Nb$_1$Te$_2$Mg$_1$ | 95.1 | 75.9 | 20.0 |
| 112 | Mo$_{12}$Nb$_1$Te$_2$Fe$_2$Sb$_2$ | 99.0 | 76.9 | 21.1 |

EXAMPLES 113 – 117

The gaseous mixture was reacted in accordance with the process of Example 71 except that metal oxide catalysts having the empirical formulas shown in Table XVIII were used. The catalysts were prepared in accordance with the process of Examples 85 – 88. The results obtained are shown in Table XVIII.

TABLE XVIII

| Example No. | Catalyst system | Isobutylene Conversion (%) | Methacrolein Selectivity (%) | Combustion rate (CO + CO$_2$) (%) |
|---|---|---|---|---|
| 113 | Mo$_{12}$Nb$_2$Te$_2$Ni$_{0.5}$ | 86.3 | 76.5 | 18.3 |
| 114 | Mo$_{12}$Nb$_2$Te$_2$V$_1$ | 88.7 | 74.2 | 23.4 |
| 115 | Mo$_{12}$Nb$_1$Te$_3$V$_{0.5}$ | 79.6 | 75.5 | 20.7 |
| 116 | Mo$_{12}$Nb$_{0.5}$Te$_1$La$_1$ | 85.8 | 75.4 | 19.8 |
| 117 | Mo$_{12}$Nb$_1$Te$_5$Th$_5$ | 85.0 | 73.6 | 17.2 |

EXAMPLE 118

The gaseous mixture was reacted in accordance with the process of Example 71 except that the metal oxide catalysts used having the empirical formula, Mo$_{12}$Ta$_1$Te$_2$Sb$_2$ were prepared with 4.42 g of tantalum oxide (Ta$_2$O$_5$) instead of niobium oxide. The results obtained indicated a 73.2% conversion of isobutylene, an 85.9% selectivity of methacrolein and a 13.3% combustion rate.

EXAMPLES 119 – 131

The gaseous mixture was reacted in accordance with the process of Example 71 except that metal oxide catalysts having the empirical formulas shown in Tables IXX, XX and XXI were used. These catalysts were prepared by using 4.42 g of tantalum oxide instead of niobium oxide in accordance with the process of Examples 72 – 88. The results obtained are shown in Tables IXX, XX and XXI. When the catalysts shown in Table IXX were used, the selectivity of methacrolein was high. When the catalysts shown in Table XX were used, the conversion of isobutylene was high.

TABLE IXX

| Example No. | Catalyst system | Isobutylene Conversion (%) | Methacrolein Selectivity (%) | Combustion rate (CO + CO$_2$) (%) |
|---|---|---|---|---|
| 119 | Mo$_{12}$Ta$_1$Te$_2$As$_3$ | 74.3 | 83.7 | 14.4 |
| 120 | Mo$_{12}$Ta$_1$Te$_1$Na$_2$ | 77.1 | 81.1 | 17.6 |
| 121 | Mo$_{12}$Ta$_1$Te$_2$Pb$_{0.5}$ | 75.3 | 82.6 | 15.1 |
| 122 | Mo$_{12}$Ta$_1$Te$_3$Ce$_2$ | 82.8 | 73.6 | 25.9 |
| 123 | Mo$_{12}$Ta$_1$Te$_1$Ca$_2$ | 79.5 | 80.4 | 14.7 |

TABLE XX

| Example No. | Catalyst system | Isobutylene Conversion (%) | Methacrolein Selectivity (%) | Combustion rate (CO + CO$_2$) (%) |
|---|---|---|---|---|
| 124 | Mo$_{12}$Ta$_1$Te$_2$Cu$_2$ | 91.5 | 70.0 | 21.2 |
| 125 | Mo$_{12}$Ta$_1$Te$_2$Cr$_1$ | 92.4 | 69.4 | 19.0 |
| 126 | Mo$_{12}$Ta$_1$Te$_2$Ag$_{0.5}$ | 91.4 | 71.5 | 24.0 |
| 127 | Mo$_{12}$Ta$_1$Te$_2$Mg$_2$Co$_{0.5}$ | 90.3 | 70.9 | 25.6 |
| 128 | Mo$_{12}$Nb$_{0.5}$Ta$_{0.5}$Te$_2$Mg$_1$ | 95.7 | 71.0 | 20.3 |
| 129 | Mo$_{12}$Nb$_1$Ta$_{0.5}$Te$_5$Mg$_2$ | 87.6 | 72.3 | 24.9 |

TABLE XXI

| Example No. | Catalyst system | Isobutylene Conversion (%) | Methacrolein Selectivity (%) | Combustion rate (CO + CO$_2$) (%) |
|---|---|---|---|---|
| 130 | Mo$_{12}$Ta$_1$Te$_3$V$_2$ | 85.1 | 70.3 | 21.5 |
| 131 | Mo$_{12}$Ta$_1$Te$_2$Th$_2$ | 87.5 | 71.0 | 22.4 | reactor was heated in a molten salt bath at 400° C. The results obtained are shown in Table XXIII.

TABLE XXIII

| Example No. | Catalyst system | Propylene Conversion (%) | Acrolein Selectivity (%) | Combustion rate (CO + CO$_2$) (%) |
|---|---|---|---|---|
| 134 | Mo$_{12}$Nb$_1$Te$_2$ | 90.3 | 82.6 | 15.3 |
| 135 | Mo$_{12}$Nb$_1$In$_2$ | 87.3 | 79.0 | 15.9 |
| 136 | Mo$_{12}$Ta$_1$Co$_2$ | 92.4 | 78.6 | 18.7 |
| 137 | Mo$_{12}$Nb$_1$Te$_2$In$_2$ | 89.8 | 80.3 | 15.0 |
| 138 | Mo$_{12}$Nb$_1$Ta$_{0.5}$Te$_2$ | 89.4 | 81.0 | 16.1 |

COMPARISON EXAMPLES III - 1 - 8

The gaseous mixture was reacted in accordance with the process of Example 76 except that the metal oxide catalysts having the empirical formulas shown in Table XXII were used. These catalysts were prepared in accordance with the process of Examples 76 - 96. The results obtained are given in Table XXII.

TABLE XXII

| Comparison Example No. | Catalyst system | Isobutylene Conversion (%) | Methacrolein Selectivity (%) | Combustion rate (CO + CO$_2$) (%) |
|---|---|---|---|---|
| III-1 | Mo$_{12}$Nb$_1$Te$_2$Sn$_2$ | 77.3 | 52.8 | 37.2 |
| III-2 | Mo$_{12}$Nb$_1$Te$_2$Pd$_2$ | 62.1 | 51.7 | 48.0 |
| III-3 | Mo$_{12}$Nb$_1$Te$_2$P$_1$ | 17.9 | 50.4 | 51.4 |
| III-4 | Mo$_{12}$Te$_2$Ce$_2$ | 48.5 | 75.2 | 29.7 |
| III-5 | Mo$_{12}$Te$_2$Co$_2$ | 25.3 | 86.0 | 12.6 |
| III-6 | Mo$_{12}$Nb$_1$Fe$_1$Sb$_2$ | 46.0 | 51.3 | 45.1 |
| III-7 | Mo$_{12}$Nb$_1$Te$_2$ | 82.3 | 70.5 | 23.0 |
| III-8 | Mo$_{12}$Ta$_1$Te$_2$ | 81.8 | 67.3 | 25.6 |

EXAMPLE 132

The gaseous mixture was reacted in accordance with the process of Example 71 except that 6 ml of a metal oxide catalyst having the empirical formula Mo$_{12}$Nb$_1$Te$_2$Sb$_2$ was used without the presence of silicon carbide. The contact time of the gas mixture was 3 seconds. The results obtained indicated a 94.5% conversion of isobutylene, an 89.1% selectivity of methacrolein and a 6.9% combustion rate.

EXAMPLE 133

The gaseous mixture was reacted in accordance with the process of Example 76 except that 6 ml of a metal oxide catalyst having the empirical formula Mo$_{12}$Nb$_1$Te$_2$Fe$_2$ of Example 85 was used, without the presence of silicon carbide. The contact time for the gas mixture was 3 seconds at a temperature of 395° C. in a molten salt bath. The results obtained indicated a 96.7% conversion of isobutylene, a 74.5% selectivity of methacrolein and an 18.1% combustion rate.

EXAMPLES 134 - 138

The gaseous mixture was reacted with the metal oxide catalysts of Examples 11, 19, 29, 66 and 67 in accordance with the process of Example 11 except that propylene was used instead of isobutylene, and the

EXAMPLES 139 - 145

The gaseous mixture was reacted in accordance with the process of Example 76 except that propylene was used instead of isobutylene. In addition, the catalysts shown in Table XXIV were used at a temperature of 400° C. in the molten salt bath. The results obtained are shown in Table XXIV.

TABLE XXIV

| Example No. | Catalyst system | Propylene Conversion (%) | Acrolein Selectivity (%) | Combustion rate (CO + CO$_2$) (%) |
|---|---|---|---|---|
| 139 | Mo$_{12}$Nb$_1$Te$_2$Sb$_2$ | 85.0 | 91.6 | 4.2 |
| 140 | Mo$_{12}$Nb$_1$Te$_2$Fe$_2$ | 98.8 | 83.6 | 12.5 |
| 141 | Mo$_{12}$Nb$_1$Te$_2$Na$_2$ | 87.2 | 85.0 | 13.1 |
| 142 | Mo$_{12}$Nb$_1$Te$_2$Cu$_2$ | 96.2 | 84.9 | 11.0 |
| 143 | Mo$_{12}$Ta$_1$Te$_2$Sb$_2$ | 87.0 | 88.4 | 10.1 |
| 144 | Mo$_{12}$Nb$_{0.5}$Ta$_{0.5}$Te$_2$Mg$_1$ | 97.2 | 86.1 | 12.9 |
| 145 | Mo$_{12}$Nb$_1$Ta$_{0.5}$Te$_5$Mg$_2$ | 94.8 | 86.8 | 13.0 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for preparing an unsaturated aldehyde having three to four carbon atoms, which comprises:
    reacting the corresponding olefin with molecular oxygen in a mole ratio of oxygen to olefin ranging from 3 : 1 to 1 : 5 in the vapor phase at a temperature of from 350°C to 520°C and a pressure of 1 to 10 atms. in the presence of a metal oxide catalyst having the formula:

$$Mo_{12}-X_a-Bi_b-Y'_c-O_d$$

wherein X is Nb, or Ta; Y' is at least one metal, but not more than 2 metals selected from the group consisting of alkali metals, Cu, Te, As, Sb and Fe; $a$ is 0.1 to 9; $b$ is 1 to 12; $c$ is 0.1 to 15; and $d$ is 37 to 114.

2. The process of claim 1, wherein the temperature of reaction is 430°C to 500°C.

3. The process of claim 1, wherein the pressure of reaction ranges from 1 to 5 atmospheres.

4. The process of claim 1, wherein the mole ratio of oxygen to olefin ranges from 3 : 1 to 1 : 1.

* * * * *